United States Patent
Takano et al.

(10) Patent No.: US 9,874,577 B2
(45) Date of Patent: Jan. 23, 2018

(54) KOLSPECIMEN TRANSPORTATION SYSTEM

(71) Applicant: HITACHI ALOKA MEDICAL, LTD., Mitaka-shi, Tokyo (JP)

(72) Inventors: Dai Takano, Mitaka (JP); Katsuhiro Suzuki, Mitaka (JP)

(73) Assignee: Hitachi, Ltd., Tokyo (JP)

( * ) Notice: Subject to any disclaimer, the term of this patent is extended or adjusted under 35 U.S.C. 154(b) by 240 days.

(21) Appl. No.: 14/411,969

(22) PCT Filed: Sep. 24, 2013

(86) PCT No.: PCT/JP2013/075724
§ 371 (c)(1),
(2) Date: Dec. 30, 2014

(87) PCT Pub. No.: WO2014/050821
PCT Pub. Date: Apr. 3, 2014

(65) Prior Publication Data
US 2015/0168433 A1  Jun. 18, 2015

(30) Foreign Application Priority Data
Sep. 26, 2012  (JP) ................................. 2012-213099

(51) Int. Cl.
*G06F 7/00* (2006.01)
*G01N 35/02* (2006.01)
(Continued)

(52) U.S. Cl.
CPC ....... *G01N 35/02* (2013.01); *G01N 35/00871* (2013.01); *G01N 35/04* (2013.01);
(Continued)

(58) Field of Classification Search
USPC ........................................................ 700/226
See application file for complete search history.

(56) References Cited

U.S. PATENT DOCUMENTS

| 7,756,603 B1 * | 7/2010 | Delaney, III ........ H01R 4/2404 |
| | | 198/459.8 |
| 2003/0044319 A1 | 3/2003 | Itoh |
| | | (Continued) |

FOREIGN PATENT DOCUMENTS

| CN | 101526545 A | 9/2009 |
| CN | 102236025 A | 11/2011 |
| | (Continued) | |

OTHER PUBLICATIONS

Office Action dated May 20, 2016, issued in counterpart Chinese Patent Application No. 2013800481359, with English translation, (17 pages).

(Continued)

*Primary Examiner* — Kyle Logan
(74) *Attorney, Agent, or Firm* — Westerman, Hattori, Daniels & Adrian, LLP

(57) ABSTRACT

A specimen transportation system is configured from linear modules, turn modules, and connection modules. The modules can freely combine with one another. Moreover, the modules form multiple paths through which specimen racks outputted from one specimen output device are transported to multiple analysis devices. When transporting a specimen rack from an upstream side to a downstream side, each module attaches a destination signal associated with the specimen rack to the specimen rack and transfers the destination signal to the downstream side. As a consequence of each module transporting the specimen rack from the upstream side to the downstream side that corresponds to the destination signal, the specimen rack becomes transported along a path that corresponds to the destination signal.

15 Claims, 9 Drawing Sheets

(51) Int. Cl.
*G01N 35/04* (2006.01)
*G01N 35/00* (2006.01)

(52) U.S. Cl.
CPC .......... *G01N 2035/00326* (2013.01); *G01N 2035/00643* (2013.01); *G01N 2035/047* (2013.01); *G01N 2035/0412* (2013.01); *G01N 2035/0462* (2013.01); *G01N 2035/0465* (2013.01)

(56) References Cited

U.S. PATENT DOCUMENTS

| | | | |
|---|---|---|---|
| 2004/0096361 A1 | 5/2004 | Matsubara et al. | |
| 2004/0253149 A1 | 12/2004 | Furino et al. | |
| 2007/0123999 A1* | 5/2007 | Raghibizadeh | A61L 2/24 700/1 |
| 2009/0223308 A1 | 9/2009 | Fukuma | |
| 2011/0244582 A1 | 10/2011 | Tatsutani | |
| 2012/0004766 A1 | 1/2012 | Stoll et al. | |

FOREIGN PATENT DOCUMENTS

| | | | |
|---|---|---|---|
| DE | 202012001229 U1 | 5/2012 | |
| GB | 2487234 A | 7/2012 | |
| JP | 09-054096 A | 2/1997 | |
| JP | 2000-55924 A | 2/2000 | |
| JP | 200088860 A | 3/2000 | |
| JP | 2000-314737 A | 11/2000 | |
| JP | 2001-099844 A | 4/2001 | |
| JP | 2001-242179 A | 9/2001 | |
| JP | 2003-098180 A | 4/2003 | |
| JP | 2003121451 A | 4/2003 | |
| JP | 2004-286748 A | 10/2004 | |
| JP | 2007-315835 A | 12/2007 | |
| JP | 2008-241513 A | 10/2008 | |

OTHER PUBLICATIONS

International Search Report dated Nov. 12, 2013, issued in corresponding application No. PCT/JP2013/075724.
Written Opinion dated Nov. 12, 2013, issued in corresponding application No. PCT/JP2013/075724.
Office Action dated Feb. 24, 2016, issued in Chinese Patent Application No. 201380048128.9, with English translation. (18 pages).
Non-Final Office Action dated Jan. 12, 2016, issued in U.S. Appl. No. 14/411,953 (21 pages).
Chinese Office Action dated Sep. 30, 2015 issued in Chinese patent application No. 201380048128.9 with English translation. (10 pages).
Chinese Office Action dated Sep. 22, 2015 issued in counterpart Chinese patent application No. 201380048135.9, with English translation (14 pages).
European Search Report dated Oct. 14, 2015 issued in European patent application No. 13840409.0 (8 pages).
European Search Report dated Oct. 14, 2015 issued in European patent application No. 13841352.1 (10 pages).
Notification Concerning Transmittal of Translation of the International Preliminary Report on Patentability (Chapter I and Chapter II) (Form PCT/IP/326) of International Application No. PCT/JP2013/075725 dated Apr. 9, 2015 with forms PCT/IB/373, PCT/IB/338 and PCT/ISA/237.

* cited by examiner

<FIRST SPECIFIC EXAMPLE OF SETTING AND CONTROL OF TURN MODULE>

| ANALYSIS DEVICE (DESTINATION) | DESTINATION CODE SIGNAL | | | TURN M (C3) | | | | TURN M (C2) | | | | TURN M (C1) | | | |
|---|---|---|---|---|---|---|---|---|---|---|---|---|---|---|---|
| | bit2 | bit1 | bit0 | DIRECTION SW | bit1 | bit0 | DIRECTION | DIRECTION SW | bit1 | bit0 | DIRECTION | DIRECTION SW | bit1 | bit0 | DIRECTION |
| E1 | L | L | H | SW1 | OFF | ON | 0 DEGREE | SW1 | OFF | ON | 0 DEGREE | SW1 | OFF | ON | 0 DEGREE |
| E2 | L | H | L | SW2 | OFF | ON | 0 DEGREE | SW2 | OFF | ON | 0 DEGREE | SW2 | ON | OFF | 90 DEGREES TO RIGHT |
| E3 | L | H | H | SW3 | OFF | ON | 0 DEGREE | SW3 | OFF | ON | 0 DEGREE | SW3 | ON | ON | 90 DEGREES TO LEFT |
| E4 | H | L | L | SW4 | OFF | ON | 0 DEGREE | SW4 | ON | OFF | 90 DEGREES TO RIGHT | SW4 | OFF | OFF | (NON-SET) |
| E5 | H | L | H | SW5 | OFF | ON | 0 DEGREE | SW5 | ON | ON | 90 DEGREES TO LEFT | SW5 | OFF | OFF | (NON-SET) |
| E6 | H | H | L | SW6 | ON | OFF | 90 DEGREES TO RIGHT | SW6 | OFF | OFF | (NON-SET) | SW6 | OFF | OFF | (NON-SET) |
| E7 | H | H | H | SW7 | ON | ON | 90 DEGREES TO LEFT | SW7 | OFF | OFF | (NON-SET) | SW7 | OFF | OFF | (NON-SET) |

FIG. 2

<SECOND SPECIFIC EXAMPLE OF SETTING AND CONTROL OF TURN MODULE>

| ANALYSIS DEVICE (DESTINATION) | DESTINATION CODE SIGNAL | | | DP SW | TURN M (C3) | | | | TURN M (C2) | | | | TURN M (C1) | | | |
|---|---|---|---|---|---|---|---|---|---|---|---|---|---|---|---|---|
| | bit2 | bit1 | bit0 | | SW1 | SW2 | SW3 | DIRECTION | SW1 | SW2 | SW3 | DIRECTION | SW1 | SW2 | SW3 | DIRECTION |
| E1 | L | L | H | bit1 | ON | OFF | OFF | 0 DEGREE | ON | OFF | OFF | 0 DEGREE | ON | OFF | OFF | 0 DEGREE |
| E2 | L | H | L | bit2 | ON | OFF | OFF | 0 DEGREE | ON | OFF | OFF | 0 DEGREE | OFF | ON | OFF | 90 DEGREES TO RIGHT |
| E3 | L | H | H | bit3 | ON | OFF | OFF | 0 DEGREE | ON | OFF | OFF | 0 DEGREE | OFF | OFF | ON | 90 DEGREES TO LEFT |
| E4 | H | L | L | bit4 | ON | OFF | OFF | 0 DEGREE | OFF | ON | OFF | 90 DEGREES TO RIGHT | OFF | OFF | OFF | (NON-SET) |
| E5 | H | L | H | bit5 | ON | OFF | OFF | 0 DEGREE | OFF | OFF | ON | 90 DEGREES TO LEFT | OFF | OFF | OFF | (NON-SET) |
| E6 | H | H | L | bit6 | OFF | ON | OFF | 90 DEGREES TO RIGHT | OFF | OFF | OFF | (NON-SET) | OFF | OFF | OFF | (NON-SET) |
| E7 | H | H | H | bit7 | OFF | OFF | ON → OFF | 90 DEGREES TO LEFT | OFF | OFF | OFF | (NON-SET) | OFF | OFF | OFF | (NON-SET) |

(IN CASE THAT ANALYSIS DEVICE (E7) HAS FAILED)

FIG. 3

< TRANSPORT POSSIBLE IN ALL MODULES >

| NODE SIGNAL ARRAY | CONNEC-TION M (D1) | CONNEC-TION M (D2) | CONNEC-TION M (D3) | TURN M (C1) | STRAIGHT-LINE M (B3) | CONNEC-TION M (D4) | CONNEC-TION M (D5) | TURN M (C2) | STRAIGHT-LINE M (B2) | CONNEC-TION M (D6) | CONNEC-TION M (D7) | TURN M (C3) | STRAIGHT-LINE M (B1) |
|---|---|---|---|---|---|---|---|---|---|---|---|---|---|
| NODE1 | ON | OFF | OFF | ON | ON | OFF | OFF | ON | ON | OFF | OFF | ON | ON |
| NODE2 | OFF | ON | OFF | ON | ON | OFF | OFF | ON | ON | OFF | OFF | ON | ON |
| NODE3 | OFF | OFF | ON | ON | ON | OFF | OFF | ON | ON | OFF | OFF | ON | ON |
| NODE4 | OFF | OFF | OFF | OFF | OFF | ON | OFF | ON | ON | OFF | OFF | ON | ON |
| NODE5 | OFF | OFF | OFF | OFF | OFF | OFF | ON | OFF | OFF | OFF | OFF | ON | ON |
| NODE6 | OFF | OFF | OFF | OFF | OFF | OFF | OFF | OFF | OFF | ON | OFF | ON | ON |
| NODE7 | OFF | OFF | OFF | OFF | OFF | OFF | OFF | OFF | OFF | OFF | ON | ON | ON |
| NODE8 | OFF | OFF | OFF | OFF | OFF | OFF | OFF | OFF | OFF | OFF | OFF | OFF | OFF |

FIG. 6

< TRANSPORT POSSIBLE IN ALL MODULES → TRANSPORT IMPOSSIBLE IN CONNECTION M (D3) >

| NODE SIGNAL ARRAY | CONNEC-TION M (D1) | CONNEC-TION M (D2) | CONNEC-TION M (D3) | TURN M (C1) | STRAIGHT-LINE M (B3) | CONNEC-TION M (D4) | CONNEC-TION M (D5) | TURN M (C2) | STRAIGHT-LINE M (B2) | CONNEC-TION M (D6) | CONNEC-TION M (D7) | TURN M (C3) | STRAIGHT-LINE M (B1) |
|---|---|---|---|---|---|---|---|---|---|---|---|---|---|
| NODE 1 | ON | OFF | OFF | ON | ON | OFF | OFF | ON | ON | OFF | OFF | ON | ON |
| NODE 2 | OFF | ON | OFF | ON | ON | OFF | OFF | ON | ON | OFF | OFF | ON | ON |
| NODE 3 | OFF | OFF | OFF | OFF | OFF | OFF | OFF | OFF | OFF | OFF | OFF | OFF | OFF |
| NODE 4 | OFF | OFF | OFF | OFF | OFF | ON | OFF | ON | ON | OFF | OFF | ON | ON |
| NODE 5 | OFF | OFF | OFF | OFF | OFF | OFF | ON | OFF | OFF | OFF | OFF | ON | ON |
| NODE 6 | OFF | OFF | OFF | OFF | OFF | OFF | OFF | OFF | OFF | ON | OFF | ON | ON |
| NODE 7 | OFF | OFF | OFF | OFF | OFF | OFF | OFF | OFF | OFF | OFF | ON | ON | ON |
| NODE 8 | OFF | OFF | OFF | OFF | OFF | OFF | OFF | OFF | OFF | OFF | OFF | OFF | OFF |

FIG. 7

< TRANSPORT POSSIBLE IN ALL MODULES → TRANSPORT IMPOSSIBLE IN TURN M (C1) >

| NODE SIGNAL ARRAY | CONNEC-TION M (D1) | CONNEC-TION M (D2) | CONNEC-TION M (D3) | TURN M (C1) | STRAIGHT-LINE M (B3) | CONNEC-TION M (D4) | CONNEC-TION M (D5) | TURN M (C2) | STRAIGHT-LINE M (B2) | CONNEC-TION M (D6) | CONNEC-TION M (D7) | TURN M (C3) | STRAIGHT-LINE M (B1) |
|---|---|---|---|---|---|---|---|---|---|---|---|---|---|
| NODE1 | ON | OFF | OFF | OFF | OFF | OFF | OFF | OFF | OFF | OFF | OFF | OFF | OFF |
| NODE2 | OFF | ON | OFF | OFF | OFF | OFF | OFF | OFF | OFF | OFF | OFF | OFF | OFF |
| NODE3 | OFF | OFF | ON | OFF | OFF | OFF | OFF | OFF | OFF | OFF | OFF | OFF | OFF |
| NODE4 | OFF | OFF | OFF | OFF | OFF | ON | OFF | ON | ON | OFF | OFF | ON | ON |
| NODE5 | OFF | OFF | OFF | OFF | OFF | OFF | ON | ON | ON | OFF | OFF | ON | ON |
| NODE6 | OFF | OFF | OFF | OFF | OFF | OFF | OFF | OFF | OFF | ON | OFF | ON | ON |
| NODE7 | OFF | OFF | OFF | OFF | OFF | OFF | OFF | OFF | OFF | OFF | ON | ON | ON |
| NODE8 | OFF | OFF | OFF | OFF | OFF | OFF | OFF | OFF | OFF | OFF | OFF | OFF | OFF |

FIG. 8

< TRANSPORT POSSIBLE IN ALL MODULES → TRANSPORT IMPOSSIBLE IN STRAIGHT-LINE M (B2) >

| NODE SIGNAL ARRAY | CONNEC-TION M (D1) | CONNEC-TION M (D2) | CONNEC-TION M (D3) | TURN M (C1) | STRAIGHT-LINE M (B3) | CONNEC-TION M (D4) | CONNEC-TION M (D5) | TURN M (C2) | STRAIGHT-LINE M (B2) | CONNEC-TION M (D6) | CONNEC-TION M (D7) | TURN M (C3) | STRAIGHT-LINE M (B1) |
|---|---|---|---|---|---|---|---|---|---|---|---|---|---|
| NODE1 | ON | OFF | OFF | ON | ON | OFF | OFF | ON | OFF | OFF | OFF | OFF | OFF |
| NODE2 | OFF | ON | OFF | ON | ON | OFF | OFF | ON | OFF | OFF | OFF | OFF | OFF |
| NODE3 | OFF | OFF | ON | ON | ON | OFF | OFF | ON | OFF | OFF | OFF | OFF | OFF |
| NODE4 | OFF | OFF | OFF | OFF | OFF | ON | OFF | ON | OFF | OFF | OFF | OFF | OFF |
| NODE5 | OFF | OFF | OFF | OFF | OFF | OFF | ON | ON | OFF | OFF | OFF | OFF | OFF |
| NODE6 | OFF | OFF | OFF | OFF | OFF | OFF | OFF | OFF | OFF | ON | OFF | ON | ON |
| NODE7 | OFF | OFF | OFF | OFF | OFF | OFF | OFF | OFF | OFF | OFF | ON | ON | ON |
| NODE8 | OFF | OFF | OFF | OFF | OFF | OFF | OFF | OFF | OFF | OFF | OFF | OFF | OFF |

FIG. 9

KOLSPECIMEN TRANSPORTATION SYSTEM

TECHNICAL FIELD

The present invention relates to a specimen transport system.

BACKGROUND ART

A specimen transport system is a system that transports a specimen, for example, housed in a specimen rack, and transports the specimen rack housing the specimen obtained from a specimen pre-treatment device or the like to an analysis device for the specimen or the like. A plurality of analysis devices, for example, are connected to the specimen transport system, and the specimen transport system transports the specimen to an analysis device, among the plurality of analysis devices, identified according to the specimen, by suitably controlling, for example, a turn unit or the like which changes a transport path of the specimen (Patent Documents 1 and 2).

In general, in a system such as a specimen transport system, a central control unit that controls and manages the overall system is provided. For example, a central control unit formed by a computer or the like controls a plurality of turn units or the like in the specimen transport system according to the specimen or the specimen rack, to transport the specimen or the specimen rack to an analysis device according to the specimen or the specimen rack.

RELATED ART REFERENCES

Patent Documents

[Patent Document 1] JP 2007-315835 A
[Patent Document 2] JP 2000-55924 A

DISCLOSURE OF INVENTION

Technical Problem

In view of the above-described related art, the present inventors have conducted research and development toward a new system structure related to the specimen transport system. In particular, the present inventors have focused attention on a system structure that would significantly reduce the control by the central control unit, and desirably, that does not require the central control unit.

The present invention has been made in the course of the research and the development as described above, and an advantage thereof is in that an improved system structure related to the specimen transport system is realized.

Solution to Problem

According to one aspect of the present invention, there is provided a specimen transport system comprising a plurality of modules, wherein a plurality of paths for transporting a specimen from upstream to downstream are formed by the plurality of modules, and the plurality of modules include an intermediate module placed partway on each path, the intermediate module comprises a unit that connects another module at each of an upstream side and a downstream side, a unit that transports a specimen which has been transported from the upstream side to the downstream side, and a unit that transmits a destination signal of the specimen acquired from the upstream side to the downstream side, and the plurality of modules can be freely combined with each other, adjacent modules are connected to each other to form the plurality of paths, and each module transports a specimen which has been transported from the upstream side to the downstream side corresponding to a destination signal of the specimen, so that the specimen is transported along a path corresponding to the destination signal.

The above-described specimen transport system includes a plurality of modules which can be freely combined with each other. Because of this, for example, a user who needs a specimen transport system can freely combine the plurality of modules to construct a desired system. In the constructed specimen transport system, each module transports the specimen which has been transported from the upstream side to the downstream side corresponding to a destination signal of the specimen, so that the specimen is transported along a path corresponding to the destination signal. Because of this, for example, a specimen transport system can be realized in which the control by a central control unit that manages the overall system is significantly reduced, or more desirably, which does not require the central control unit.

According to another aspect of the present invention, preferably, when the intermediate module transports the specimen which has been transported from the upstream side to the downstream side, the intermediate module transmits, along with the specimen, the destination signal correlated to the specimen to the downstream side.

According to another aspect of the present invention, preferably, the intermediate module includes a branch module in which a plurality of downstream modules can be connected at the downstream side, and the branch module comprises a unit that selects, based on the destination signal, a downstream module corresponding to the destination signal from among the plurality of downstream modules.

According to another aspect of the present invention, preferably, the specimen is housed in a specimen rack, and the branch module comprises a unit that rotates the specimen rack which has been transported from the upstream side, and selects a downstream module corresponding to the destination signal by rotating the specimen rack according to the destination signal correlated to the specimen rack.

According to another aspect of the present invention, preferably, for each of the plurality of paths formed by the free combination of the plurality of modules, a code that identifies the path is correlated, the destination signal is configured to identify one of the plurality of codes for the plurality of paths, and the branch module selects a downstream module of the path corresponding to the code from among the plurality of downstream modules correlated to a plurality of rotational directions by rotating the specimen rack in a rotational direction corresponding to the code identified by the destination signal.

According to another aspect of the present invention, preferably, the branch module comprises a unit that can freely set a rotational direction of the specimen rack for each of the codes correlated to the plurality of paths according to a free combination of the plurality of modules including the branch module.

Advantageous Effects of Invention

According to various aspects of the present invention, an improved system structure related to the specimen transport system can be realized. For example, according to a preferable configuration of the present invention, a user who requires the specimen transport system can freely combine a plurality of modules to construct a desired system. In addition, a specimen transport system can be realized in which control by a central control unit that manages the overall system is significantly reduced, and, more desirably, the central control unit is not required.

BRIEF DESCRIPTION OF DRAWINGS

FIG. 2 is a diagram showing a first specific example configuration of setting and control of a turn module.

FIG. 3 is a diagram showing a second specific example configuration of setting and control of a turn module.

FIG. 6 is a diagram showing a specific example configuration in which transport is possible in all modules.

FIG. 7 is a diagram showing a specific example configuration in which transport at a connection module is not possible.

FIG. 8 is a diagram showing a specific example configuration in which transport at a turn module is not possible.

FIG. 9 is a diagram showing a specific example configuration in which transport at a straight-line module is not possible.

BEST MODE FOR CARRYING OUT THE INVENTION

Figure 1:
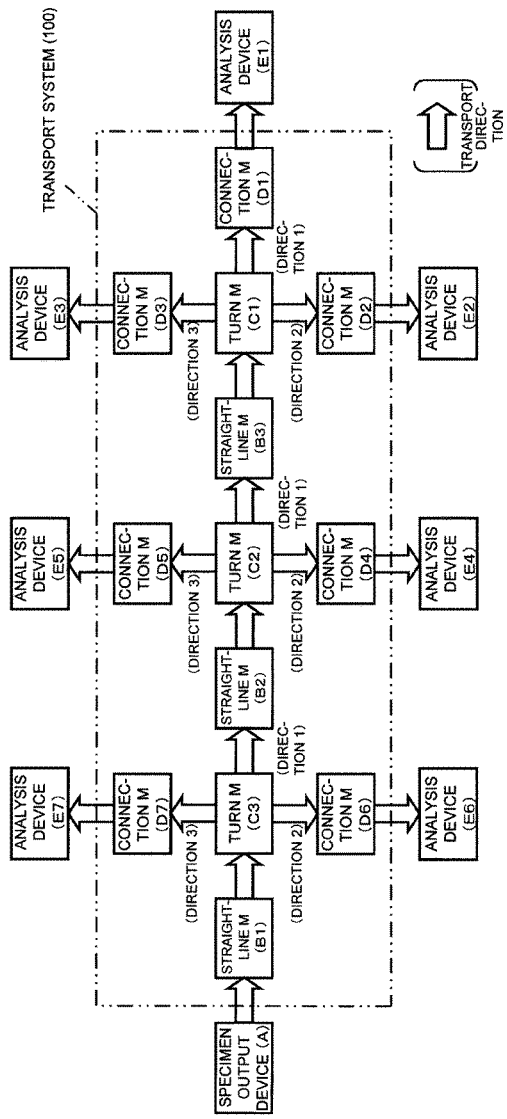
FIG. 1 is a diagram showing an overall structure of a specimen transport system preferable in practicing the present invention.

FIG. 1 is a diagram showing an overall structure of a specimen transport system 100 preferable in practicing the present invention. The specimen transport system 100 is a system that transports a specimen which is output from a specimen output device A such as a specimen pre-treatment device to a plurality of analysis devices E (E1~E7). The specimen is housed in a container such as, for example, a test tube, one or more containers housing the specimens are housed in a specimen rack, and the specimen transport system 100 transports the specimen rack.

The specimen transport system 100 of FIG. 1 is formed by a plurality of modules. In FIG. 1, a "straight-line M" shows a straight-line module, a "turn M" shows a turn module, and a "connection M" shows a connection module. Thus, in the specific example configuration shown in FIG. 1, the specimen transport system 100 includes straight-line modules B (B1~B3), turn modules C (C1~C3), and connection modules D (D1~D7).

The plurality of modules can be freely combined with each other, adjacent modules are structurally and communicatively connected to each other, and the plurality of modules form a plurality of paths to transport a specimen rack which is output from one specimen output device A to the plurality of analysis devices E (E1~E7). The specimen transport system 100 shown in FIG. 1 is merely an example configuration of a combination of the plurality of modules, and alternatively, the specimen transport system 100 may be formed by a combination different from the example configuration of FIG. 1.

The straight-line module B is a module that moves the specimen rack which has been transported in from an upstream side in a straight line and transports the specimen rack out to a downstream side. For example, the straight-line module B1 moves in a straight line the specimen rack which is output from the specimen output device A and transported to the straight-line module B1, and transports the specimen rack out to the turn module C3.

The straight-line module B includes a conveyer of a straight line shape, and moves the specimen rack while placing the specimen rack on the straight-line-shaped conveyer. For example, a stopper of the specimen rack and a sensor for detecting presence/absence of the specimen rack are provided at an entrance (upstream side) of the conveyer, and a stopper and a sensor are provided, for example, also at an exit (downstream side) of the conveyer.

The turn module C is a module that rotationally moves the specimen rack which is transported in from the upstream side, and transports the specimen rack out to a desired downstream side corresponding to the specimen rack. For example, the turn module C3 rotationally moves a specimen rack which is transported in from the straight-line module B1 to a rotational direction (directions 1~3) corresponding to the specimen rack, and transports the specimen rack out to one of the connection module D6, the connection module D7, and the straight-line module B2.

The turn module C includes a turntable, places the specimen rack which has been transported in from the upstream side on the turn table to rotationally move the specimen rack to a direction according to the specimen rack, and transports the specimen rack out to the downstream side corresponding to one of the directions 1~3. For example, a stopper of the specimen rack and a sensor that detects presence/absence of the specimen rack are provided at an entrance (upstream side) of the turntable, and a stopper and a sensor are provided, for example, also at an exit (downstream side) of the turntable.

The connection module D is a module that transports the specimen rack which has been transported in from the upstream side out to the analysis device E at the downstream side. For example, the connection module D6 transports the specimen rack which has been transported in from the direction 2 of the turn module C3 to the analysis device E6.

FIG. 1 shows, as a representative example of the plurality of modules, the straight-line modules B, the turn modules C, and the connection modules D. Alternatively, modules other than these modules may be provided as necessary. For example, a buffer module that temporarily retracts the transported specimen rack and that changes the order of transport of the specimen rack may be provided. Alternatively, straight-line modules having different lengths from each other or turn modules having a different number of directions from each other may be provided.

Furthermore, as the branch module, in place of or in addition to the turn module, for example, a traverse transport module or an elevator transport module may be provided.

The traverse transport module is a module that slides, within a horizontal plane, the specimen rack which has been transported in from the upstream side, and transports the specimen rack out to a desired downstream side corresponding to the specimen rack. The traverse transport module slides, for example, the specimen rack which has been transported in from the upstream side in the horizontal plane in a direction perpendicular to the transported direction of the specimen rack, and transports the specimen out to the desired downstream side. On the other hand, the elevator transport module is a module that moves the specimen rack which has been transported in from the upstream side in a vertical direction (up-and-down direction), and transports the specimen rack out to the desired downstream side corresponding to the specimen rack.

Branch modules that can select a desired downstream side without rotating the specimen rack such as the traverse transport module and the elevator transport module may be used. Alternatively, a branch module may be used in which the rotation, the sliding in the horizontal plane, and the movement in the vertical direction of the specimen rack are suitably combined.

The specimen transport system 100 of FIG. 1 transports the specimen rack based on a destination code signal correlated to each specimen rack, along a path indicated by the destination code signal. When transporting the specimen rack which has been transported in from the upstream side out to the downstream side, the modules of the specimen transport system 100 transmit the destination code signal correlated to the specimen rack to the downstream side along with the specimen rack. For example, the destination code signal is transmitted in parallel to the transporting of the specimen rack.

In particular, the turn module C rotates the specimen rack in one of the directions 1~3 according to the destination code signal which is transmitted along with the specimen rack, to select a downstream side corresponding to the destination code signal. The turn module C has a function which can freely set the rotational direction of the specimen rack for each code indicated by the destination code signal, according to a free combination of the plurality of modules including the turn module C. A setting of the rotational direction for the turn module C and control of the rotational direction in the turn module C will now be described.

FIG. 2 is a diagram showing a first specific example configuration of the setting and control of the turn module. FIG. 2 shows a specific example configuration of the setting of the rotational direction for three turn modules C (C1~C3) in the specimen transport system 100 of FIG. 1 and the control of the rotational direction in the turn modules C. The plurality of analysis devices E (E1~E7) in FIG. 2 also correspond to the analysis devices E in the specimen transport system 100 of FIG. 1.

In FIG. 2, the destination code signal is formed by 3 bits, and each code identified by the 3 bits is correlated to each of the analysis devices E. In other words, each code is correlated to the path to each analysis device E. For example, when the code is shown in the order of bit2, bit1, and bit0, a destination code signal (L, L, H) is correlated to the analysis device E1, and a destination code signal (L, H, L) is correlated to the analysis device E2.

In the first specific example configuration of FIG. 2, a plurality of direction switches (direction SWs) are provided for the turn modules C. The direction SWs SW1~SW7 are correlated to the codes of the destination code signal. For example, SW1 is correlated to the destination code signal (L, L, H), and SW2 is correlated to the destination code signal (L, H, L).

The direction SWs SW1~SW7 are formed by setting bits of 2 bits for determining the rotational direction. The setting bits of each of the direction SWs are set, for example, according to a constructed system and by the system constructor who constructs the specimen transport system 100 (FIG. 1) by freely combining the plurality of modules.

With the setting bits of 2 bits in each direction SW, the rotational direction of the specimen rack corresponding to the direction SW is set. In the first specific example configuration of FIG. 2, if the setting bits of the direction SW are shown in the order of bit1, and bit0, setting bits of (OFF, ON) indicate a rotational direction of 0 degree, setting bits of (ON, OFF) indicate a rotational direction of 90 degrees to the right, and setting bits of (ON, ON) indicate a rotational direction of 90 degrees to the left.

The setting related to the direction SW of the turn module C shown in FIG. 2 corresponds to the transport paths in the specimen transport system 100 of FIG. 1. Thus, the control of the turn module C in the first specific example configuration of FIG. 2 will be described with reference to FIG. 1.

For example, when a specimen rack to be analyzed by the analysis device E1 is output from the specimen output device A, the straight-line module B1 correlates a destination code signal of (L, L, H) to the specimen rack, transports the specimen rack to the turn module C3, and transmits the destination code signal (L, L, H) to the turn module C3.

The turn module C3 uses, of the plurality of direction SWs, setting bits of (OFF, ON) of SW1 corresponding to the destination code signal (L, L, H). Thus, the rotational direction of the specimen rack is controlled to the direction 1 which is 0 degree, and the specimen rack is transported out to the straight-line module B2. The straight-line module B2 transports the specimen rack which has been transported to the turn module C2, and transmits to the turn module C2 the destination code signal (L, L, H) correlated to the specimen rack.

The turn module C2 uses, of the plurality of direction SWs, setting bits of (OFF, ON) of SW1 corresponding to the destination code signal (L, L, H). Thus, the rotational direction of the specimen rack is controlled to the direction 1 which is 0 degree, and the specimen rack is transported out to the straight-line module B3. The straight-line module B3 transports the specimen rack which has been transported to the turn module C1, and transmits to the turn module C1 the destination code signal (L, L, H) correlated to the specimen rack.

The turn module C1 uses, of the plurality of direction SWs, setting bits of (OFF, ON) of SW1 corresponding to the destination code signal (L, L, H). Thus, the rotational direction of the specimen rack is controlled to the direction 1 which is 0 degree, and the specimen rack is transported out to the connection module D1. The connection module D1 transports to the analysis device E1 the specimen rack which has been transported.

In this manner, the specimen rack is transported from the straight-line module B1 at the furthest upstream side to the connection module D1 at the furthest downstream side along the path from the specimen output device A to the analysis device E1, formed in the specimen transport system 100.

In addition, when, for example, a specimen rack to be analyzed by the analysis device E6 is output from the specimen output device A, the straight-line module B1 correlates a destination code signal of (H, H, L) to the specimen rack, transports the specimen rack out to the turn module C3, and transmits the destination code signal (H, H, L) to the turn module C3.

The turn module C3 uses, of the plurality of direction SWs, setting bits of (ON, OFF) of SW6 corresponding to the destination code signal (H, H, L). Thus, the rotational direction of the specimen rack is controlled to the direction 2 which is 90 degrees to the right, and the specimen rack is transported out to the connection module D6. The connection module D6 transports to the analysis device E6 the specimen rack which has been transported.

In this manner, the specimen rack is transported from the straight-line module B1 at the furthest upstream side to the connection module D6 at the furthest downstream side, along a path from the specimen output device A to the analysis device E6, formed in the specimen transport system 100. Because the turn modules C2 and C1 are not used for the path from the specimen output device A to the analysis device E6, in the turn modules C2 and C1, setting bits of SW6 corresponding to the destination code signal (H, H, L) of the analysis device E6 are set to (OFF, OFF), or to a non-set state.

Specific example configurations of the control from the specimen output device A to the analysis device E1 and to the analysis device E6 have been described. For other analysis devices E (E2~E5, E7) also, the turn modules C are controlled according to the setting related to the direction SWs of the turn modules C shown in FIG. 2, and the specimen rack is transported from the specimen output device A to a desired analysis device E.

FIG. 3 is a diagram showing a second specific example configuration of the setting and control of the turn modules. FIG. 3 shows a specific example configuration of the setting of the rotational direction for the three turn modules C (C1~C3) in the specimen transport system 100 of FIG. 1, and the control of the rotational directions of the turn modules C. A plurality of analysis device E (E1~E7) of FIG. 3 also correspond to the analysis devices E in the specimen transport system 100 of FIG. 1.

Similar to the first specific example configuration of FIG. 2, in the second specific example configuration of FIG. 3 also, the destination code signal is formed with 3 bits, and codes identified by 3 bits are correlated to the analysis devices E. In other words, each code is correlated to the path to the corresponding analysis device E.

In the second specific example configuration of FIG. 3, dip switches (DPSW) of 3 rows from SW1 to SW3 are provided for the turn modules C. Each switch row (SW1~SW3) is formed with a dip switch of 7 bits. Each bit (bit1~bit7) of the dip switch is correlated to a respective code of the destination code signal. For example, the bit1 of the dip switch is correlated to the destination code signal (L, L, H), and the bit2 of the dip switch is correlated to the destination code signal (L, H, L).

In the second specific example configuration of FIG. 3, with a setting of the dip switches (DPSW) of 3 rows from SW1 to SW3, the rotational directions of the specimen rack at the turn modules C are determined. The dip switch (DPSW) of 3 rows is set, for example, according to a constructed system and by a system constructor who constructs the specimen transport system 100 (FIG. 1) by freely combining the plurality of modules.

In the second specific example configuration of FIG. 3, if the setting states of the dip switch are shown in the order of SW1, SW2, and SW3, a setting state of (ON, OFF, OFF) indicates a rotational direction of 0 degree, a setting state of (OFF, ON, OFF) indicates a rotational direction of 90 degrees to the right, and a setting state of (OFF, OFF, ON) indicates a rotational direction of 90 degrees to the left.

The setting related to the dip switch for the turn modules C shown in FIG. 3 also corresponds to the transport paths in the specimen transport system 100 of FIG. 1. Thus, a control of the turn modules C in the second specific example configuration of FIG. 3 will be described with reference to FIG. 1.

For example, when a specimen rack to be analyzed by the analysis device E3 is output from the specimen output device A, the straight-line module B1 correlates a destination code signal (L, H, H) to the specimen rack, transports the specimen rack out to the turn module C3, and transmits the destination code signal (L, H, H) to the turn module C3.

The turn module C3 uses, of the dip switch of 7 bits, a setting state of (ON, OFF, OFF) of the bit3 corresponding to the destination code signal (L, H, H). Thus, the rotational direction of the specimen rack is controlled to the direction 1 which is 0 degree, and the specimen rack is transported out to the straight-line module B2. The straight-line module B2 transports the specimen rack which has been transported to the turn module C2, and transmits to the turn module C2 the destination code signal (L, H, H) correlated to the specimen rack.

The turn module C2 uses, of the dip switch of the 7 bits, a setting state of (ON, OFF, OFF) of the bit3 corresponding to the destination code signal (L, H, H). Thus, the rotational direction of the specimen rack is controlled to the direction 1 which is 0 degree, and the specimen rack is transported out to the straight-line module B3. The straight-line module B3 transports the specimen rack which has been transported to the turn module C1, and transmits to the turn module C1 the destination code signal (L, H, H) correlated to the specimen rack.

The turn module C1 uses, of the dip switch of 7 bits, a setting state of (OFF, OFF, ON) of the bit3 corresponding to the destination code signal (L, H, H). Thus, the rotational direction of the specimen rack is controlled to the direction 3 which is 90 degrees to the left, and the specimen rack is transported out to the connection module D3. The connection module D3 transports the specimen rack which has been transported to the analysis device E3.

In this manner, the specimen rack is transported from the straight-line module B1 at the furthest upstream side to the connection module D3 at the furthest downstream side, along a path from the specimen output device A to the analysis device E3, formed in the specimen transport system 100.

In addition, for example, when a specimen rack to be analyzed by the analysis device E7 is output from the specimen output device A, the straight-line module B1 correlates a destination code signal of (H, H, H) to the specimen rack, transports the specimen rack out to the turn module C3, and transmits the destination code signal (H, H, H) to the turn module C3.

The turn module C3 uses, of the dip switch of the 7 bits, a setting state of (OFF, OFF, ON) of the bit7 corresponding to the destination code signal (H, H, H). Thus, the rotational direction of the specimen rack is controlled to the direction 3 which is 90 degrees to the left, and the specimen rack is transported out to the connection module D7. The connection module D7 transports to the analysis device E7 the specimen rack which has been transported.

In this manner, the specimen rack is transported from the straight-line module B1 at the furthest upstream side to the connection module D7 at the furthest downstream side along a path from the specimen output device A to the analysis device E7, formed in the specimen transport system 100. Because the turn modules C2 and C1 are not used in the path from the specimen output device A to the analysis device E7, in the turn modules C2 and C1, setting states of the bit7 corresponding to the destination code signal (H, H, H) of the analysis device E7 are set to (OFF, OFF, OFF), or to the non-set state.

Specific example configurations of the controls from the specimen output device A to the analysis device E3 and to the analysis device E7 have been described. For the other analysis devices E (E1, E2, E4~E6) also, the turn modules C are controlled according to the setting states related to the dip switch of the turn modules C shown in FIG. 3, and the specimen rack is transported from the specimen output device A to a desired analysis device E.

In the setting state of FIG. 3, when the analysis device E7 becomes non-usable due to, for example, failure or the like, the setting state of the bit7 of the dip switch of the turn module C3 may be changed from (OFF, OFF, ON) to (OFF, OFF, OFF). With such a process, in the turn module C3, the setting state of the bit7 corresponding to the destination code signal (H, H, H) of the analysis device E7 is set to (OFF, OFF, OFF) or to the non-set state, and a control is applied so that the specimen rack is not transported out to the analysis device E7. When the analysis device E7 again becomes useable, the setting state of the bit7 of the dip switch of the turn module C3 may be returned to (OFF, OFF, ON).

In this manner, the specimen rack which is output from the specimen output device A is transported to the analysis device E corresponding to the destination code signal. Next, a structure of each module used in the specimen transport system 100 of FIG. 1 will be described.

Figure 4:
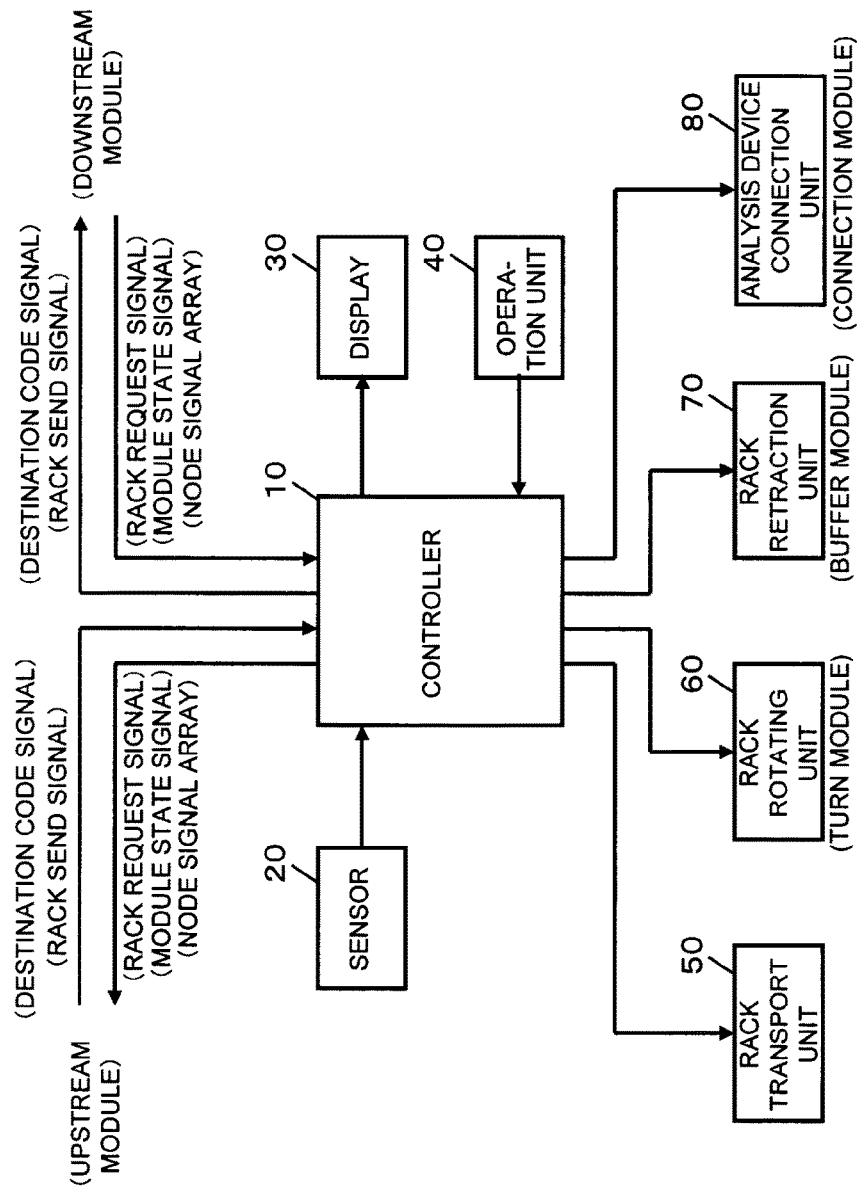
FIG. 4 is a diagram showing a structure of each module.

FIG. 4 is a diagram showing a structure of each module. Each module has a connection unit for connecting another module or another device at an upstream side or a downstream side. Each module further has a rack transport unit 50 formed by, for example, a conveyer and a stopper, and transports the specimen rack which is transported from the upstream side to the downstream side.

On an entrance (upstream side) of the conveyer which moves the specimen rack with the specimen rack placed thereon, a sensor 20 which detects presence/absence of the specimen rack is provided, and, for example, a sensor 20 is also provided on an exit (downstream side) of the conveyer. For example, based on a detection result of the sensors 20, the presence/absence of the specimen rack in each module is checked.

A controller 10 controls elements in each module. Because it is sufficient for the controller 10 to control only the elements in the module having the controller 10, for example, the controller 10 can be realized using a microcomputer or the like of a relatively small scale, without using a CPU or the like of a relatively large scale equipped in a computer or the like.

A setting state in the module or the like is displayed on a display 30. The display 30 may be realized by a display device such as, for example, an LCD, or may alternatively be realized by a simple structure that shows the setting state of the direction SW (FIG. 2) or the dip switch (FIG. 3) with an LED or the like.

An operation unit 40 accepts an operation of a user, in particular, a system constructor who constructs the specimen transport system. The operation unit 40 may be realized by a touch panel or the like along with the display 30, or may alternatively be realized by a plurality of switches that switch ON/OFF of the direction SW (FIG. 2) or the dip switch (FIG. 3).

A structure common to the modules has been described. In addition, according to the type of the module, for example, for a turn module, a rack rotating unit 60 formed with a turntable or the like for rotating the specimen rack is provided; for a buffer module, a rack retraction unit 70 for temporarily retracting the specimen rack to change the order of transport of the specimen rack is provided; and for the connection module, an analysis device connection unit 80 in which an analysis device is connected at the downstream side is provided.

Moreover, each module exchanges various signals with an upstream module connected at the upstream side and a downstream module connected at the downstream side. For example, a rack request signal, a module state signal, and a node signal array are sent from the module to the upstream module, and from the downstream module to the module. In addition, the destination code signal and a rack send signal are transmitted from the upstream module to the module, and from the module to the downstream module.

Figure 5:
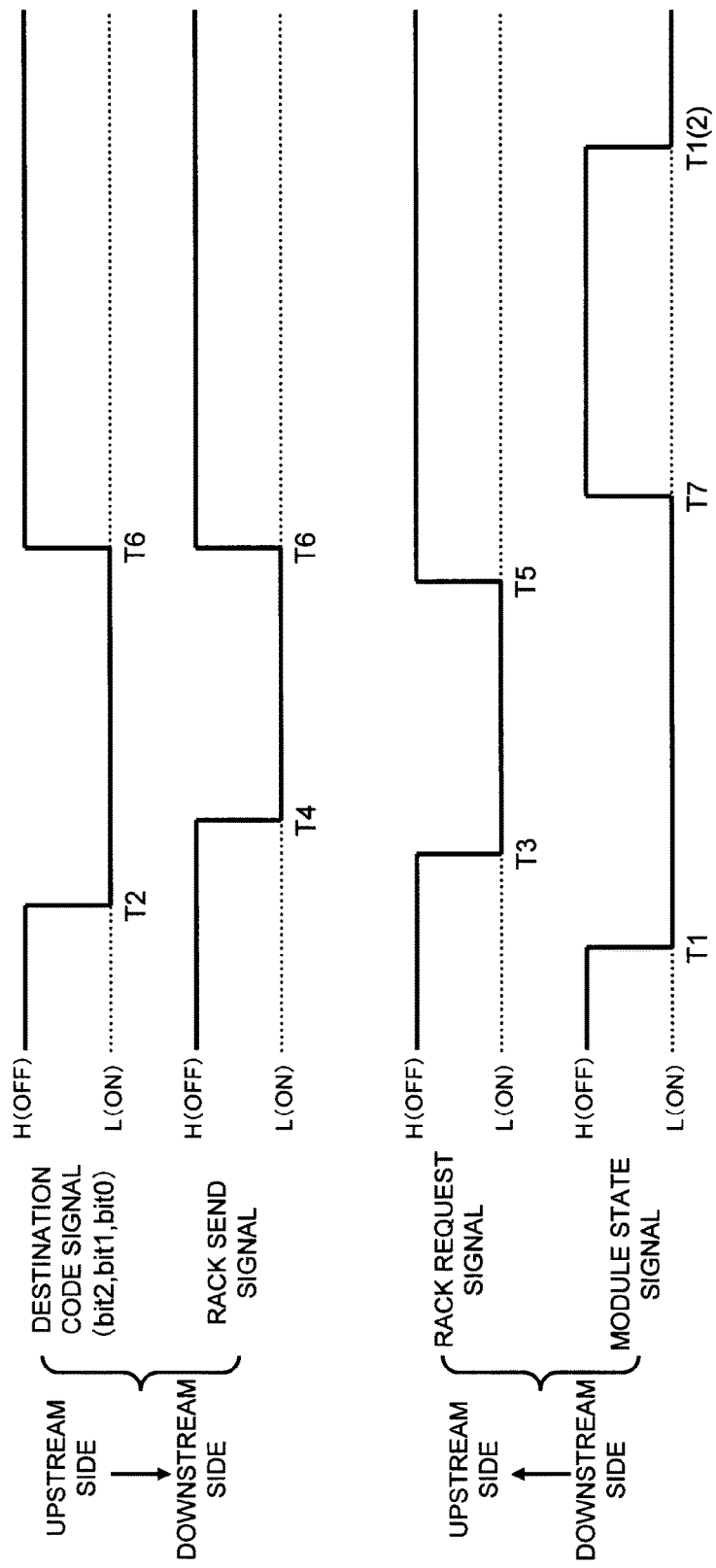
FIG. 5 is a timing chart of signals exchanged between modules.

FIG. 5 is a timing chart of signals exchanged between the modules when the specimen rack is transferred. In the timing chart of FIG. 5, various signals exchanged during transfer of the specimen rack between an upstream side module and a downstream side module which are connected to each other are shown. In other words, FIG. 5 shows the destination code signal, the rack send signal, the rack request signal, and the module state signal. These signals are all set to H (OFF) in, for example, an initialization process of the system immediately after the specimen transport system 100 (FIG. 1) is powered on (ON).

In the transfer of the specimen rack, first, the module state signal is referred to. The module state signal is a signal which indicates whether or not the module outputting the signal is in a state where the specimen rack can be accepted. The module state signal is set, for example, to H (OFF) when the specimen rack cannot be accepted, and to L (ON) when the specimen rack can be accepted.

In the example configuration shown in FIG. 5, the module state signal which is output from the downstream side module to the upstream side module is set to L (ON) at time T1. In other words, the example configuration shows that the downstream side module assumes a state where the module can accept the specimen rack at time T1. When the module state signal is set to L (ON), the upstream side module outputs a destination code signal correlated to the specimen rack.

The destination code signal is formed by, for example, 3 bits, and each code identified with 3 bits is correlated to the respective analysis device E (refer to FIGS. 2 and 3). In the example configuration of FIG. 5, the destination code signal which is output from the upstream side module to the downstream side module is set to L (ON) at time T2. In other words, at least one bit of the destination code signal formed by 3 bits is set to L (ON) at time T2.

When the destination code signal is set to L (ON), the downstream side module judges whether or not the module can accept a specimen rack corresponding to the destination code signal, and, when the module can accept the specimen rack, the rack request signal is set to L (ON). For example, the module judges whether or not the specimen rack can be accepted based on a node signal array to be described later in detail. In the example configuration of FIG. 5, the rack request signal which is output from the downstream side module to the upstream side module is set to L (ON) at time T3.

When the upstream side module confirms that the rack request signal is set to L (ON), the upstream side module sets the rack send signal to L (ON). The rack send signal is a signal which indicates a timing of transporting out the specimen rack. In the example configuration of FIG. 5, the rack send signal which is output from the upstream side module to the downstream side module is set to L (ON) at time T4. The upstream side module starts transporting out the specimen rack by activating the rack transport unit at time T4, and the downstream side module also starts transporting in the specimen rack by activating the rack transport unit at time T4.

In this manner, the transporting out and in of the specimen rack are started between the upstream side module and the downstream side module, and, when the transporting in of the specimen rack is completed at the downstream side module, the downstream side module completes the transport-in operation of the specimen rack, and sets the rack request signal to H (OFF). In the example configuration of FIG. 5, the rack request signal which is output from the downstream side module to the upstream side module is set to H (OFF) at time T5.

When the upstream side module confirms that the rack request signal is set to H (OFF), the upstream side module completes the transport-out operation of the specimen rack, and sets the rack send signal to H (OFF) and all of the destination code signals to H (OFF). In the example configuration of FIG. 5, the rack send signal and the destination code signal which are output from the upstream side module to the downstream side module are set to H (OFF) at time T6.

When the downstream side module confirms that the rack send signal is set to H (OFF), the downstream side module sets the module state signal to H (OFF). In the example configuration of FIG. 5, the module state signal which is output from the downstream side module to the upstream side module is set to H (OFF) at time T7. In other words, the timing chart shows a state in which the downstream side module cannot accept a next specimen rack at the time T7 because the specimen rack is present in the downstream side module.

When the specimen rack present in the downstream side module is transported out to the module at a further downstream side, the downstream side module which has completed transporting out the specimen rack assumes a state in which the next specimen rack can be accepted from the upstream side module, and thus, the module state signal is again set to L (ON). In the example configuration of FIG. 5, the module state signal is set to L (ON) at time T1(2), the downstream side module becomes a state where the next specimen rack can be accepted, and the next specimen rack is transferred between the upstream side and downstream side modules.

By sequentially transferring the specimen rack by the above-described exchange of the signals between the upstream side module and the downstream side module, a plurality of specimen racks are sequentially transported to the analysis devices E corresponding to the destination code signals of the specimen racks.

Next, the node signal array used in the specimen transport system 100 of FIG. 1 will be described. The plurality of modules forming the specimen transport system 100 can be freely combined with each other, adjacent modules are structurally and communicatively connected to each other, and, with such a configuration, the specimen transport system 100 of FIG. 1, for example, is constructed. That is, a plurality of paths for transporting the specimen rack, which is output from one specimen output device A, to a plurality of analysis devices E (E1~E7) are formed. For each path, a node signal indicating possibility/impossibility of transport at the path is correlated, and a node signal array is formed from a plurality of node signals for the plurality of paths.

Each module of the specimen transport system 100 transmits, under the control of the controller 10 (FIG. 4) of the module, the node signal array acquired from the downstream side to the upstream side, and changes, in the node signal array to be transmitted, the node signal of the path including the module to transport impossible when transport in that module becomes impossible. Using the node signal array, processes such as retention of the specimen rack in the specimen transport system 100 or the like are handled.

FIGS. 6-8 are diagrams for explaining the node signal array in the specimen transport system 100 of FIG. 1 and a specific example control using the node signal array. The specific example control will now be described based on FIGS. 6 and 8, and with reference to FIG. 1.

FIG. 6 is a diagram showing a specific example control when all of the modules can transport. The node signal array is made of a plurality of nodes. Each node is correlated to each of the plurality of paths in the specimen transport system 100.

In the specific example control of FIG. 6, a node 1 is correlated to a path to the analysis device E1; that is, a path from the straight-line module B1 at the furthest upstream side to the connection module D1 at the furthest downstream side. A node 2 is correlated to a path to the analysis device E2; that is, a path from the straight-line module B1 at the furthest upstream side to the connection module D2 at the furthest downstream side. Similarly, nodes 3-7 are correlated to the paths to the analysis devices E3~E7, respectively. In the specific example control of FIG. 6, the node 8 is not being used.

All of the nodes from node 1 to node 8 forming the node signal array are set to OFF, for example, in a system initialization process immediately after the specimen transport system 100 is powered on (ON).

The node signal array is sequentially transmitted from the downstream side module to the upstream side module. For example, in the example configuration of FIGS. 6 and 1, the connection module D1 is a module at the furthest downstream side in the path of the node 1 corresponding to the analysis device E1, checks whether or not the analysis device E1 connected at the downstream side can accept a specimen rack, and sets the node 1 corresponding to the analysis device E1 to ON (transport possible) when the specimen rack can be accepted. In the example configuration of FIG. 6, the node 1 is set to ON (transport possible) by the connection module D1.

The connection module D2 is a module at the furthest downstream side in the path of the node 2 corresponding to the analysis device E2, checks whether or not the analysis device E2 can accept a specimen rack, and sets the node 2 corresponding to the analysis device E2 to ON (transport possible) when the specimen rack can be accepted. In the example configuration of FIG. 6, the node 2 is set to ON (transport possible) by the connection module D2.

Similarly, the connection modules D3~D7 check the states of the analysis devices E3~E7 connected thereto, and set the corresponding node to ON (transport possible) when the specimen rack can be accepted. In the example configuration of FIG. 6, all of the analysis devices E1~E7 can accept the specimen rack, and each of the connection modules D1~D7 sets the corresponding node of the node 1~the node 7 to ON (transport possible).

The node signal array is sequentially transmitted from the downstream side module to the upstream side module. For example, in the example configuration of FIGS. 6 and 1, the connection modules D1~D3 are connected to the downstream side of the turn module C1. Because of this, the node signal array is transmitted from each of the connection modules D1~D3 to the turn module C1, and the turn module C1 merges the node signal arrays acquired from the connection modules D1~D3, and transmits the node signal array to the upstream side of the turn module C1.

Specifically, in the example configuration of FIG. 6, because each of the connection modules D1~D3 sets the corresponding node of the node 1~the node 3 to ON, the turn module C1 produces a node signal array setting all nodes of the node 1~the node 3 to ON, and transmits the produced node signal array to the straight-line module B3 at the upstream side. The straight-line module B3 transmits the node signal array transmitted from the turn module C1 to the turn module C2 at the upstream side.

In the turn module C2, the connection modules D4 and D5 and the straight-line module B3 are connected at the downstream side. Because of this, node signal arrays are transmitted from the connection modules D4 and D5 and the straight-line module B3 to the turn module C2. The turn module C2 merges the node signal arrays acquired from the connection modules D4 and D5 and the straight-line module B3, and transmits the node signal array to the upstream side of the turn module C2.

Specifically, in the example configuration of FIG. 6, the connection modules D4 and D5 set the corresponding nodes of the node 4 and node 5 to ON, and the node 1~the node 3 are set to ON in the node signal array acquired from the straight-line module B3. Because of this, the turn module C2 produces a node signal array setting all nodes of the node 1~the node 5 to ON, and transmits the produced node signal array to the straight-line module B2 at the upstream side. The straight-line module B2 transmits the node signal array transmitted from the turn module C2 to the turn module C3 at the upstream side.

In the turn module C3, the connection modules D6 and D7 and the straight-line module B2 are connected at the downstream side. Because of this, node signal arrays are transmitted from the connection modules D6 and D7 and the straight-line module B2 to the turn module C3. The turn module C3 merges the node signal arrays acquired from the connection modules D6 and D7 and the straight-line module B2, and transmits the node signal array to the upstream side of the turn module C3.

Specifically, in the example configuration of FIG. 6, the connection modules D6 and D7 set the corresponding node of the node 6 and the node 7 to ON, and the node 1~the node 5 are set to ON in the node signal array acquired from the straight-line module B2. Because of this, the turn module C3 produces a node signal array setting all node of the node 1~the node 7 to ON, and transmits the produced node signal array to the straight-line module B1 at the upstream side.

The straight-line module B1 placed at the furthest upstream side requests, to the specimen output device A connected at the upstream side, a specimen rack to be transported to each path while referring to the node signal array transmitted from the downstream side. The straight-line module B1 requests a specimen rack to be transported to a path corresponding to a node which is set to ON (transport possible) in the node signal array while avoiding a request of a specimen rack to be transported to a path corresponding to a node which is set to OFF (transport impossible) in the node signal array.

Specifically, in the example configuration of FIG. 6, all paths of the node 1~the node 7 are set to ON (transport possible), and all of the analysis devices E1~E7 can accept a specimen rack. Therefore, the straight-line module B1 can request to the specimen output device A a specimen rack related to all paths of the node 1~the node 7.

FIG. 7 is a diagram showing a specific example configuration where the connection module cannot transport. FIG. 7 shows a specific example configuration where a state of transport impossibility has occurred in the connection module D3 from the state where all of the modules can transport (FIG. 6).

In the example configuration of FIG. 6 described above, the connection module D3 checks the state of the analysis device E3 connected at the downstream side, and has set the node 3 to ON (transport possible) because the analysis device E3 can accept the specimen rack.

However, when, for example, analysis is being executed in the analysis device E3 for the specimen rack which is already transported and the next specimen rack cannot be accepted, or when there is some kind of trouble in the analysis device E3 and the specimen rack cannot be accepted, as shown in FIG. 7, the connection module D3 sets the node 3 to OFF (transport impossible). When there is some kind of trouble in the connection module D3 itself and the specimen rack cannot be accepted also, the connection module D3 sets the node 3 to OFF (transport impossible).

When the node 3 is set to OFF in the node signal array acquired from the connection module D3, in the turn module C1 which merges the node signal arrays of the connection modules D1~D3 also, the node 3 is set to OFF, and the node signal array merged at the turn module C1 is transmitted to the turn module C2 via the straight-line module B3.

When the node 3 is set to OFF in the node signal array acquired from the straight-line module B3, in the turn module C2 which merges the node signal arrays from the straight-line module B3 and the connection modules D4 and D5 also, the node 3 is set to OFF, and a node signal array merged at the turn module C2 is transmitted to the turn module C3 via the straight-line module B2.

When the node 3 is set to OFF in the node signal array acquired from the straight-line module B2, in the turn module C3 that merges the node signal arrays from the straight-line module B2 and the connection modules D6 and D7 also, the node 3 is set to OFF, and a node signal array merged at the turn module C3 is transmitted to the straight line module B1.

The straight-line module B1 placed at the furthest upstream side requests, to the specimen output device A which is connected at the upstream side, a specimen rack to be transported to each path while referring to the node signal array transmitted from the downstream side. The straight-line module B1 requests a specimen rack to be transported to a path corresponding to a node which is set to ON (transport possible) in the node signal array, while avoiding a request of a specimen rack to be transported to a path corresponding to a node which is set to OFF (transport impossible) in the node signal array.

In the example configuration of FIG. 7, because the path of the node 3 is set to OFF, the straight-line module B1 requests specimen racks related to paths of nodes which are set to ON, while avoiding a request of a specimen rack related to the path of the node 3. The specimen rack for which the request is avoided is temporarily put to hold, for example, in the specimen output device A. When the specimen transport system 100 is transporting a specimen rack of the node 3 at the time when the path of the node 3 is set to OFF, the specimen rack is transported to a location to which the specimen rack can be transported; for example, to the connection module D3. In other words, by configuring the system such that the specimen rack is, as much as possible, not retained at the upstream side of the specimen transport system 100, it becomes possible to secure paths to the analysis devices E1, E2, and E4~E7.

FIG. 8 is a diagram showing a specific example configuration where the turn module cannot transport. FIG. 8 shows a specific example configuration where a state of transport impossibility has occurred in the turn module C1 from the state where all of the modules can transport (FIG. 6).

In the example configuration of FIG. 6 described above, the turn module C1 has produced a node signal array in which all nodes of the node 1~the node 3 are set to ON because the connection modules D1~D3 at the downstream side have set the corresponding nodes of the node 1~the node 3 to ON.

However, when, for example, some kind of trouble has occurred in the turn module C1 and the turn module C1 assumes a state in which the specimen rack cannot be accepted, the turn module C1 sets all nodes of the paths including the turn module C1 to OFF. Specifically, as shown in FIG. 8, the turn module C1 sets all of the node 1~the node 3 corresponding to the paths to the connection modules D1~D3 (analysis devices E1~E3) in which the turn module C1 is involved to OFF (transport impossible). The node signal array merged at the turn module C1 is transmitted to the turn module C2 via the straight-line module B3.

When the node 1~the node 3 in the node signal array acquired from the straight-line module B3 are set to OFF, in the turn module C2 which merges the node signal arrays from the straight-line module B3 and the connection modules D4 and D5 also, the node 1 the node 3 are set to OFF, and a node signal array merged at the turn module C2 is transmitted to the turn module C3 via the straight-line module B2.

When the node 1~the node 3 are set to OFF in the node signal array acquired from the straight-line module B2, in the turn module C3 which merges the node signal arrays from the straight-line module B2 and the connection modules D6 and D7 also, the node 1~the node 3 are set to OFF, and a node signal array merged at the turn module C3 is transmitted to the straight-line module B1.

The straight-line module B1 which is placed at the furthest upstream side requests, to the specimen output device A which is connected at the upstream side, a specimen rack to be transported to each path while referring to the node signal array transmitted from the downstream side. The straight-line module B1 requests a specimen rack to be transported to a path corresponding to a node which is set to ON in the node signal array while avoiding a request of a specimen rack to be transported to a path corresponding to a node which is set to OFF in the node signal array.

In the example configuration of FIG. 8, because the paths of the node 1~the node 3 are set to OFF, the straight-line module B1 requests a specimen rack related to a path of a node which is set to ON while avoiding a request of specimen racks related to the paths of the node 1~the node 3. The specimen rack for which the request is avoided is, for example, temporarily put to hold in the specimen output device A. When the specimen transport system 100 is transporting a specimen rack of the node 1~the node 3 at the time when the paths of the node 1~the node 3 are set to OFF, the specimen rack is transported to a location where the transport is possible; for example, to the straight-line module B3. In other words, by employing a configuration so that, as much as possible, the specimen rack is not retained in the upstream side of the specimen transport system 100, it becomes possible to secure paths to the analysis devices E4~E7.

FIG. 9 is a diagram showing a specific example configuration where the straight-line module cannot transport. FIG. 9 shows a specific example configuration where a state of transport impossibility has occurred in the straight-line module B2 from the state where all of the modules can transport (FIG. 6).

In the example configuration of FIG. 6 described above, the straight-line module B2 has acquired the node signal array setting all of the node 1~the node 5 to ON, from the turn module C2 at the downstream side.

However, when, for example, some kind of trouble occurs in the straight-line module B2 and the specimen rack cannot be accepted, the straight-line module B2 sets all nodes of the paths including the straight-line module B2 itself to OFF. Specifically, as shown in FIG. 9, the straight-line module B2 sets all of the node 1~the node 5 corresponding to the paths to the connection modules D1~D5 (analysis devices E1~E5) in which the straight-line module B2 is involved to OFF (transport impossible). The node signal array changed at the straight-line module B2 is transmitted to the turn module C3.

When the node 1~the node 5 are set to OFF in the node signal array acquired from the straight-line module B2, in the turn module C3 which merges the node signal arrays from the straight-line module B2 and the connection modules D6 and D7 also, the node 1~the node 5 are set to OFF, and a node signal array merged at the turn module C3 is transmitted to the straight-line module B1.

The straight-line module B1 which is placed at the furthest upstream side requests, to the specimen output device A connected at the upstream side, a specimen rack to be transported to each path while referring to the node signal array transmitted from the downstream side. The straight-line module B1 requests a specimen rack to be transported to a path corresponding to a node which is set to ON in the node signal array while avoiding a request of a specimen rack to be transported to a path corresponding to a node which is set to OFF in the node signal array.

In the example configuration of FIG. 9, because the paths of the node 1~the node 5 are set to OFF, the straight-line module B1 requests a specimen rack related to a path of the node which is set to ON while avoiding a request of a specimen rack related to the paths of the node 1~the node 5. The specimen rack for which the request is avoided is, for example, temporarily put to a hold in the specimen output device A. When the specimen transport system 100 is transporting a specimen rack for the node 1~the node 5 at the time when the paths of the node 1~the node 5 are set to OFF, the specimen rack is transported to a location where the transport is possible, and a configuration is employed in which, as much as possible, the specimen rack is not retained at the upstream side of the specimen transport system 100.

A preferable configuration of the present invention has been described. However, the above-described embodiment is merely a simple exemplification in all points of view, and does not limit the scope of the present invention. Various modified configurations are included in the present invention within the scope and spirit of the present invention.

EXPLANATION OF REFERENCE NUMERALS

B STRAIGHT-LINE MODULE; C TURN MODULE; D CONNECTION MODULE; 100 SPECIMEN TRANSPORT SYSTEM

The invention claimed is:

1. A specimen transport system having a plurality of variably combinable modules, comprising:
  a plurality of modules configured to be combined to create a plurality of paths for transporting a specimen from an upstream one of said plurality of modules to downstream ones of said plurality of modules, wherein the plurality of modules include an intermediate module placed in between adjacent ones of said plurality of modules along at least one of said paths,
  the intermediate module having a connector that connects an upstream one of said modules at an upstream side of the intermediate module and a connector that connects a downstream one of said modules at a downstream side of the intermediate module, a transporter that transports a specimen from the upstream side of the intermediate module to the downstream side of the intermediate module, and a controller configured to control transmission of a destination signal for the specimen received from the upstream one of said modules at the upstream side of the intermediate module to the downstream one of said modules at the downstream side of the intermediate module and configured to control transmission of a node signal, indicating a possibility of transport along a path downstream of said intermediate module, received from the downstream one of said modules at the downstream side of the intermediate module to the upstream one of said modules at the upstream side of the intermediate module, whereby the plurality of modules are configured to be variably combined with each other with different ones of said plurality of modules variably positioned adjacent one another, with adjacent modules connected to each other to create variability in the plurality of paths, each module downstream along said plurality of paths transports a specimen from the upstream side of that module to the downstream side of that module based on a destination signal corresponding to the specimen received from a module upstream from that module so that the specimen is transported along a path corresponding to the destination signal, and wherein said system is configured to correlate for each of the paths, a node signal indicating possibility/impossibility of transport at that path and to form a node signal array made of a plurality of the node signals for the plurality of paths, and the intermediate module is configured to transmit under control of the controller a node signal array acquired from the downstream one of said modules at the downstream side of the intermediate module to the upstream one of said modules at the upstream side of the intermediate module.

2. The specimen transport system according to claim 1, wherein when the intermediate module transports the specimen, the intermediate module transmits, along with the specimen, the destination signal correlated to the specimen to the downstream one of said modules at the downstream side of the intermediate module.

3. The specimen transport system according to claim 1, wherein the intermediate module is a branch module in which a plurality of downstream modules can be connected at the downstream side of the intermediate module, and the branch module includes a controller that is configured to select, based on the destination signal, a downstream module corresponding to the destination signal from among the plurality of downstream modules.

4. The specimen transport system according to claim 3, wherein the specimen is housed in a specimen rack, and the controller is configured to select a downstream module corresponding to the destination signal correlated to the specimen rack which has been transported from the upstream side of the branch module, and transports the specimen rack to the selected downstream module.

5. The specimen transport system according to claim 4, wherein the branch module comprises a rotator that rotates the specimen rack which has been transported from the upstream side of the branch module, and that is configured to select a downstream module corresponding to the destination signal by rotating the specimen rack according to the destination signal correlated to the specimen rack.

6. The specimen transport system according to claim 5, wherein said system is configured to correlate a plurality of codes that each respectively identifies a respective path of the plurality of paths, and the branch module is configured to set a rotational direction of a specimen rack for each code correlated to each of the plurality of paths according to the particular combination of the plurality of modules including the branch module.

7. The specimen transport system according to claim 1, wherein said system is configured to correlate a plurality of codes that each respectively identifies a respective path of the plurality of paths, and the destination signal is configured to identify one of the plurality of codes for a respective path of the plurality of paths.

8. The specimen transport system according to claim 7, wherein the intermediate module is a branch module in which a plurality of downstream modules can be connected at the downstream side of the intermediate module, and the branch module includes a controller that is configured to select a downstream module of a path corresponding to a code identified by the destination signal from among the plurality of downstream modules.

9. The specimen transport system according to claim 8, wherein the specimen is housed in a specimen rack, and the controller is configured to select a downstream module of a path corresponding to a code identified by the destination signal correlated to a specimen rack which has been transported from the upstream side of the branch module, and transports the specimen rack to the selected downstream module.

10. The specimen transport system according to claim 9, wherein the branch module includes a rotator that rotates a specimen rack which has been transported from the upstream side.

11. The specimen transport system according to claim 10, wherein the controller is configured to select the downstream module of the path corresponding to a code by rotating the specimen rack in a rotational direction corresponding to the code identified by the destination signal correlated to the specimen rack which has been transported from the upstream side of the branch module.

12. The specimen transport system according to claim 11, wherein the branch module is configured to variably set a rotational direction according to a code for each of the codes correlated to the plurality of paths according to a variable combination of the plurality of modules including the branch module.

13. The specimen transport system according to claim 1, wherein the intermediate module is configured to:

change, when the intermediate module becomes unable to transport, the node signal, in the node signal array to be transmitted, of the path including the intermediate module to transport impossible.

14. The specimen transport system according to claim 13, wherein
the intermediate module is a branch module in which a plurality of downstream modules can be connected at a downstream side of the intermediate module, and
the branch module is configured to merge node signal arrays acquired from the plurality of downstream modules connected at the downstream side of the intermediate module and to transmit the node signal array to the upstream module at the upstream side of the intermediate module.

15. The specimen transport system according to claim 14, wherein
the plurality of modules include a furthest upstream module placed at a furthest upstream side in each path, and a furthest downstream module placed at a furthest downstream side of each path,
the furthest upstream module being configured to refer to a node signal array acquired from a downstream module connected at the downstream side of the furthest upstream module, and to request a specimen to be transported to a path for which the node signal indicates possibility of transport while avoiding a request of a specimen to be transported to a path for which the node signal indicates impossibility of transport, and
the furthest downstream module being configured to change, when an analysis device connected at the downstream side cannot accept a specimen, a node signal of a path to the analysis device via the furthest downstream module to transport impossible.

* * * * *